US006983178B2

(12) United States Patent
Fine et al.

(10) Patent No.: US 6,983,178 B2
(45) Date of Patent: Jan. 3, 2006

(54) PROBE FOR USE IN NON-INVASIVE MEASUREMENTS OF BLOOD RELATED PARAMETERS

(75) Inventors: Ilya Fine, Rehovot (IL); Alexander Finarov, Rehovot (IL)

(73) Assignee: Orsense Ltd., Rehovot (IL)

( * ) Notice: Subject to any disclaimer, the term of this patent is extended or adjusted under 35 U.S.C. 154(b) by 6 days.

(21) Appl. No.: 10/049,959

(22) PCT Filed: Mar. 15, 2001

(86) PCT No.: PCT/IL01/00250

§ 371 (c)(1),
(2), (4) Date: Jun. 26, 2002

(87) PCT Pub. No.: WO01/67946

PCT Pub. Date: Sep. 20, 2001

(65) Prior Publication Data

US 2002/0173709 A1   Nov. 21, 2002

(30) Foreign Application Priority Data

Mar. 15, 2000  (IL) ............................................. 135077

(51) Int. Cl.
*A61B 5/00* (2006.01)

(52) U.S. Cl. ..................... 600/335; 600/323; 600/344
(58) Field of Classification Search ................. 600/323, 600/322, 344, 334–335
See application file for complete search history.

(56) References Cited

U.S. PATENT DOCUMENTS 5,833,602 A * 11/1998 Osemwota .................. 600/310
6,019,716 A * 2/2000 Forestell et al. .............. 494/21
6,115,621 A * 9/2000 Chin ........................... 600/323
6,213,952 B1 * 4/2001 Finarov et al. .............. 600/491
6,222,189 B1 * 4/2001 Misner et al. ............... 600/335
6,285,894 B1 * 9/2001 Oppelt et al. ............... 600/335

* cited by examiner

Primary Examiner—Max F. Hindenburg
Assistant Examiner—Matthew J. Kremer
(74) Attorney, Agent, or Firm—Browdy & Neimark, P.L.L.C.

(57) ABSTRACT

A probe device for use in non-invasive optical measurements of at least one parameter of the patient's blood. The probe device comprises a finger holder in the form of a clip member that secures a fingertip between its clamping legs. The probe device supports a measuring unit for applying optical measurements to a measurement location on the finger and carries a pressurizing assembly operable for applying controllably variable, substantially under-systolic pressure to the finger in the vicinity of the measurement location. Several measurement sessions are performed at the measurement location with at least two different 3 wavelength of incident light to detect light response of the medium and generate measured data indicative thereof, and the pressure applied to the vicinity of the measurement location is simultaneously varied during measurements. The light response of the medium corresponding to different wavelength of the incident light and different pressure values during measurements. The light response of the medium corresponding to different wavelength of the incident light and different pressure values is analyzed, and an optimal pressure value is determined, so as to utilize the corresponding light response of the medium for deriving therefrom the at least on blood parameter.

13 Claims, 7 Drawing Sheets

PROBE FOR USE IN NON-INVASIVE MEASUREMENTS OF BLOOD RELATED PARAMETERS

FIELD OF THE INVENTION

This invention is generally in the field of non-invasive optical measurement techniques for measuring blood parameters, and relates to a probe to be applied to a patient's finger.

BACKGROUND OF THE INVENTION

Non-invasive techniques for measuring various blood parameters, such as blood oxygen saturation and the concentration of substances contained in the blood (hemoglobin, glucose and other substances) have become very popular, since they do not require the withdrawal of a blood sample from a patient's body. Optical monitoring techniques of the kind specified typically utilize the detection of light transmitted or reflected from the location on the patient's body under measurement, and are based on spectrophotometric measurements enabling the indication of the presence of various blood constituents based on known spectral behaviors of these constituents. Most of these techniques utilize a measurement optical device or probe, designed in a manner to be attached to the patient's finger, which includes an optical assembly for irradiating the finger with light and detecting its light response.

U.S. Pat. No. 5,810,723 discloses an apparatus for the non-invasive monitoring of a patient's carboxyhemoglobin level. The patient breathes oxygen to saturate his blood hemoglobin prior to detection. The apparatus utilizes a clamp with arms holding the patient's finger: one arm supports a light emitting source and the other supports a detector. A microprocessor controls the measurements and processes the detected signals.

U.S. Pat. No. 5,638,816 and its continuation, U.S. Pat. No. 5,860,919, disclose an apparatus for the non-invasive monitoring of blood parameters by applying pressure to the patient's finger, thus inducing an active pulse therein. The induced change of blood volume enables a better signal-to-noise ratio to be obtained.

U.S. Pat. No. 5,782,757 discloses a measuring devices in the form of disposable, folded adhesive sensors with optics embedded therein. The probe is designed so as to fit comfortably onto a patient's fingertip.

All the conventional devices of the kind specified are aimed at measuring enhanced optical pulsatile signals caused by the changes in the volume of the blood containing medium (finger). It is known that a regular optical pulsatile signal is typically 2–3% of the total transmission. The above devices are capable of obtaining the enhanced pulsatile signal that reach 8–10% of the total light transmission intensity. This enhancement of the natural pulsatile signal is a boundary of all conventional techniques of the kind specified.

A different technique is disclosed in a PCT application, International Publication No. WO 99/65384, assigned to the assignee of the present application. This is an occlusion based technique, where the measured signals are not pulsatile. According to this technique, the state of blood cessation is created in a medium under measurement, and measurements are taken during this state. This enables to obtain a significantly enhanced light response of the medium, as compared to that of the previously described techniques dealing with the pulsatile signals. To create such a state of blood cessation, over-systolic pressure needs to be applied to the patient's finger at a location upstream of the area under measurement, with respect to the direction of normal blood flow. Once the blood flow cessation state is established, the optical characteristics start to change dramatically, such that they differ from those of the fleshy medium with a normal blood flow by about 25 to 45%, and sometimes even by 60%. At least two timely separated measurement sessions are performed, each including at least two measurements with different wavelengths of incident radiation. None of the conventional probes is suitable for these purposes. A probe in the form of a finger holder, suitable for applying over systolic pressure to a first location on the patient's finger and applying optical measurements to a second location downstream of the first location, is disclosed in a co-pending U.S. application Ser. No. 09/407,390, assigned to the assignee of the present application.

SUMMARY OF THE INVENTION

There is a need in the art to further improve non-invasive measurements of blood parameters, by providing a novel probe device to be used in non-invasive optical measurements enabling the application of a variable controlled pressure to the patient's organ (e.g., his finger) in the vicinity of a measurement location.

It is a major object of the present invention to provide such a device that optimizes the finger tissue and blood volume, thereby providing conditions for measurements with maximum accuracy.

It was found by the inventors that the accuracy of the measured signal can be improved even more by applying certain under-systolic pressure (0–250 mmHg) to a region in the vicinity of a measurement location. This pressure, required for significantly improving the accuracy of measurements, may be different for different patients, depending inter alia on the internal blood pressure of the specific patient, and individual peculiarity of the finger size, shape and physiological conditions. This optimal pressure value depends also on the rigidity of the construction of probe device itself. Therefore means should be provided enabling to controllably vary the magnitude of the applied pressure.

Generally speaking, the present invention provides an active sensing means that enables to select an optimal pressure for a specific patient, such that the application of this pressure provides an optimal optical measurement signal for deriving therefrom the correct value of the parameter to be measured. In other words, the present invention enables to adjust the conditions of a measurement location on the patient's organ to the optimal signal determination.

Thus, according to one broad aspect of the present invention, there is provided a method of non-invasive optical measurement of at least one parameter of the patient's blood, the method comprising the steps of:

(a) applying a probe device to the patient's blood perfused fleshy medium, wherein the probe device carries an optical measurement unit and a pressurizing assembly operable to apply controllably varying substantially under-systolic pressure to a measurement location on said medium;

(b) performing several measurement sessions to a measurement location on said medium to detect light response of the medium and generate measured data indicative thereof, and simultaneously varying the pressure applied to the vicinity of said measurement location, wherein each measurement session utilizes at least two different wavelength of incident light;

(c) analyzing the light response of the medium corresponding to different wavelengths of the incident light and different pressure values, and determining an optimal pressure value, so as to utilize the corresponding light response of the medium for deriving therefrom said at least one blood parameter.

Preferably, the method according to the invention also comprises the application of over-systolic pressure to a location upstream of the measurement location, with respect to the direction of normal blood flow in the medium, so as to create the state of blood flow cessation. In this case, the measurements are taken during this state. Several time-separated measurement sessions can be performed either during the single blood-cessation state, or during the sequential blood cessation state. The latter operational mode is actually the so-called "multiple-occlusion", obtained by sequentially applying and releasing the over-systolic pressure.

Parameters that can be measured include oxygen saturation and the concentration of substance in blood, such as hemoglobin, glucose, etc. The present invention may utilize a calibration stage, during which various patients undergo measurements, and calibration curves corresponding to different blood parameters as functions of the applied under-systolic pressure are plotted.

The wavelengths of incident light are selected in accordance with the parameter to be measured. Preferably, several different wavelengths are sequentially applied, so as to obtain data from which different blood parameters can be derived within the same measurement session.

The probe device according to the invention utilizes a finger holder carrying a measurement unit and a pressurizing assembly, all operated by a control system. The measurement unit typically comprises illumination and detection systems, arranged so as to detect reflected or transmitted light, as the case may be. The pressurizing assembly is designed so as to apply variable controlled pressure to the tissue in the vicinity of the measurement location.

Generally, the probe device may be associated with any other suitable patient's organ, such as his hand or wrist. If the patient's hand is considered, the rigid connector engages the patient's arm to prevent its folding at the elbow joint. It is more practical, however, to apply the device to the patient's finger.

The finger holder is in the form of a clip securing the fingertip between its legs and carrying the measurement unit. The clip may be formed with one pair or two pairs of legs. The four-leg design advantageously enables to provide four-sided support for the finger, thereby preventing its folding at the distal phalanx. A pair of manipulating arms is used for opening and closing the clip when putting the device in operation. In the case of the two-legged design, the extensions of the legs serve as the manipulating arms. In the case of the four-legged design, the manipulating arms are coupled to the legs through any suitable mechanism, enabling the simultaneous pivotal movement of all the legs.

The pressurizing assembly is of a pneumatic type. According to one embodiment of the invention, the pressurizing assembly comprises a bellow-like cushion, which is interconnected between the manipulating arms by its opposite ends and is coupled to the drive operated by the control system. The expansion and squeezing of the sleeve thus operates the pivotal movement of the manipulating arms, thereby weakening or enhancing the clamping effect of the clip legs. According to another embodiment of the invention, the pressurizing assembly comprises a balloon-like flat cushion attached to the inner side of the clip between its upper leg and a flexible cushion-like member contacting the patient's finger, so as to press on the finger portion below the clip. In this case a locking device is provided to prevent the opening of the clip. According to yet another embodiment of the invention, the pressurizing assembly comprises a ring-like cushion attached to the inner side of the clip so as to wrap the finger, when putting the device into operation. The control system operates the expansion and squeezing of the cushion.

There is thus provided according to another aspect of the invention, a probe device to be used in non-invasive optical measurements of a patient's blood parameters, the probe device comprising a finger holder having a clip member that secures a fingertip between its clamping legs, wherein the finger holder supports a measuring unit for applying optical measurements to a measurement location on the finger, and carries a pressurizing assembly operable for applying controllably variable, substantially under-systolic pressure to the finger in the vicinity of said measurement location.

The probe device may be used with a pulse oxymeter, wherein the application of the controllably varied under-systolic pressure enables to derive more information from measured signals. This information contains the maximal amplitude of a pulsatile signal and/or AC/DC ratio.

Thus, according to yet another aspect of the present invention, there is provided a pulse-oxymeter utilizing the above probe device and a control system that operates the pressurizing assembly and the measurement unit and generates data indicative of the measured parameters.

Preferably, the probe device also comprises an additional pressurizing assembly, which may also be of a pneumatic type, and operated by the same drive means as the above-described pressurizing assembly. The additional pressurizing assembly is aimed at applying over-systolic pressure, so as to cause the state of blood flow cessation and enable the occlusion-based measurements. The over-systolic pressure is applied to a location upstream of the measurement location, with respect to a normal blood flow direction.

Preferably, the additional pressurizing assembly is coupled to the clip through a substantially rigid connector engaging the finger along its middle phalanx and proximal intephalangeal joint. This is associated with the fact that occlusion-based measurements are non-volumetric, and the changes in volume of blood in the finger portion undergoing measurement are undesirable for such measurements. However, it is a natural tendency of the finger under pressure (over-systolic pressure) to fold at the proximal intephalangeal joint, thereby causing undesirable changes in blood volume. By providing a substantially rigid support for the finger at the region of the middle phalanx during measurement, such undesirable folding can be avoided.

The present invention also provides an optical measurement device for the non-invasive measurement of patient's blood parameters, the device comprising:

a finger holder for attaching to the patient's finger, wherein the finger holder is in the form of a clip member, which secures a fingertip between its clamping legs and supports a measuring unit in a manner allowing to apply optical measurements to a measurement location on the finger;

a first pressurizing assembly operable for applying over-systolic pressure to a location on the patient's finger upstream of said measurement location with respect to a normal blood flow direction, so as to create a state of blood flow cessation at said measurements location;

a second pressurizing assembly associated with the finger holder and operable for applying desired pressure to the finger in the vicinity of said measurement location; and a control system selectively operating the first and second pressurizing assembly, and selectively operating the measuring unit, the control system having a processor that received data indicative of measured signals coming from the measuring unit and analyzes said data.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figure 1:
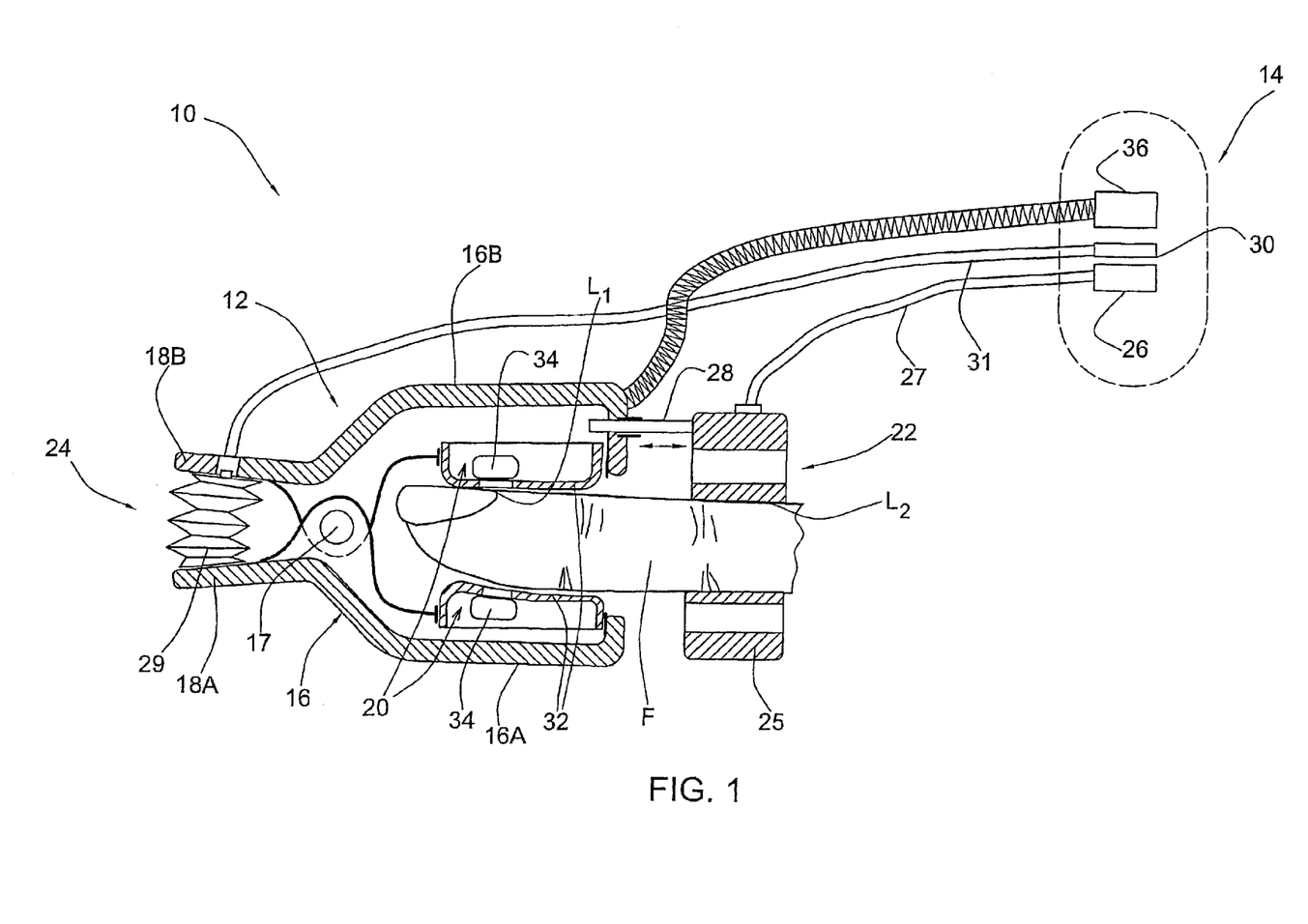
FIG. 1 is a schematic illustration of a probe device according to one embodiment of the invention.

Referring to FIG. 1, there is illustrated a probe device, generally designated 10, applied to a patient's finger F for performing the non-invasive measurement of the patient's blood parameters, such as oxygen saturation, blood pressure or the concentration of various substances, such as hemoglobin, glucose, cholesterol and other analyte concentrations. The probe 10 is in the form of a finger holder 12 mounted on the patient's finger F, and is coupled to a control system 14.

The finger holder 12 is in the form of a clip member 16 having clamping legs—two legs 16A and 16B in the present example, pivotal about an axis 17, for securing the patient's finger F therebetween. A pair of manipulating arms 18A and 18B operates the pivotal movement of the clamping legs to attach the device to the patient's finger. The clip member 16 carries a measuring unit 20 mounted on its inner side so as to apply optical measurements to a measurement location $L_1$ on the patient's finger. Further provided in the probe device 10 is a pressurizing assembly 24 associated with the finger holder 12. In the present example, the probe device 10 is used for occlusion-based measurements. To this end, an additional pressurizing assembly 22 is provided for applying over-systolic pressure to the blood perfuzed fleshy medium therebelow. When dealing with pulse-oxymetry based measurements, the provision of the pressurizing assembly 22 could be omitted.

The pressurizing assembly (first assembly) 22 is composed of an air cushion cuff 25 in the form of a ring wrapping the patient's finger F and a pneumatic drive 26 coupled to the cuff 25 through a pipe 27. The ring wraps the finger F at a location $L_2$ upstream of the measurement location $L_1$ with respect to the direction of the normal blood flow. The pressurizing assembly 22, when actuated, operates to apply over-systolic pressure, e.g., 220–300 mmHg (generally, adjustable for each specific patient), at the location $L_2$, thereby causing the state of blood-flow cessation at the measurement location $L_1$. The cuff 25 is coupled to the clip member 16 by a substantially rigid connector 28. The rigid plate-like connector 28 engages the finger along its middle phalanx, preventing its folding at the proximal intephalangeal joint, thereby avoiding undesirable changes in blood volume. The connector 28 is shaped like a plate, and is designed in a manner to enable reciprocating sliding movement of the cuff 25 relative to the clip 16 along the axis of the connector 28. This enables to adjust the length of the entire finger holder 12 to that of the finger of a specific patient. For example, although not specifically shown, the plate-like connector could be formed with an elongated slot, while the cuff-ring be formed with a projection installed in this slot for reciprocating sliding movement along its axis.

In the present example of FIG. 1, the other (second) pressurizing assembly 24 is composed of a bellow-like air cushion 29 coupled to its pneumatic drive 30 through a pipe 31. By appropriately expanding or squeezing the cushion 29, the clamping affect of the legs is adjusted so as to apply a desired pressure onto the patient's finger in the vicinity of the measurement location $L_1$. It should, however, be noted that a common pneumatic drive could operate both the cushions 25 and 29.

As further shown in FIG. 1, a pair of flexible, thermo-conductive pads 32 (or pads with built-in heaters), made for example of rubber or silicone, is provided at the inner surfaces of the legs 16A and 16B. The pads 32 are coupled to a power source (not shown) operated by a corresponding utility of the control system 14 for applying appropriate, substantially low voltages (e.g., in the range 1V–24V) to the pads 32, enabling heating the finger portion at the measurement location up to 36–38°. The heating ability of the device increases the accuracy of the non-invasively derived blood-related parameters. The substantially low voltage supply required for heating is, on the one hand, acceptable for medical devices, and, on the other hand, allows for using batteries, thereby rendering the entire device conveniently portable.

The measuring unit 20 does not form part of the present invention, and therefore need not be specifically illustrated and described, except to note that it comprises such main constructional parts as illumination and detection assemblies, generally at 34, and generates data indicative of the light response of the finger. Generally, the illumination and detection assemblies could be accommodated either at one side of the finger when operating in a reflection mode, or at opposite sides of the finger when operating in a transmission mode. These reflected or transmitted signals present light response of the finger to incident radiation. According to the occlusion-based technique disclosed in the above-indicated PCT application, the measuring unit provides illumination of the finger with at least two different wavelengths, and detects light transmitted therethrough.

Preferably, the illumination unit comprises a plurality of light sources (e.g., LEDs) for illuminating the measurement location with a plurality of different wavelengths in the near infrared spectra. This enables the simultaneous determination of different blood parameters. The wavelengths are selected in accordance with the parameter to be determined. For example, if the hemoglobin concentration is to be determined, the selected wavelengths are in the ranges, where the absorption properties of the hemoglobin and plasma are more sharply expressed, namely are in the ranges 600–1000 nm and 1100–1400 nm. If the oxygen saturation is to be determined, the selected wavelengths lie in the range where the difference in the absorption of hemoglobin (Hb) and oxyhemoglobin ($HbO_2$) are more sharply expressed, namely are in the ranges 600–780 nm (where the difference in the sensitivity of $HbO_2$ and Hb is maximal) and 820–980 nm (reference range). When dealing with the glucose concentration, the spectral ranges of 1500–1600 nm may be added to the above-mentioned range of 600–1300 nm for selecting the operational wavelengths.

The generated data indicative of the detected light (light response of the illuminated medium) is transmitted to the control system 14 for processing and analyzing. To this end, the control system 14 includes a processor 36 operated by suitable software for analyzing the detected signals and determining the desired parameter of the patient's blood, as will be described more specifically further below with reference to FIGS. 4a–4d.

Thus, each of the drives 26 and 30 of the first and second pressurizing assemblies 22 and 24, respectively, whilst being actuated by a corresponding utility of the control system 14, operates to apply required pressure to the finger portion at locations $L_2$ and $L_1$. The pressurizing assembly 24 is first actuated, and when a certain under-systolic pressure is applied to the vicinity of the measurement location $L_1$, the control system 14 actuates the pressurizing assembly 22 to apply the over-systolic pressure to the location $L_2$. When the blood flow cessation state is created, the control system 14 operates the measurement unit 20 to illuminate the measurement location with different wavelengths and detect the light response. The application of over-systolic pressure (location $L_2$) is maintained for a period of time, so as not to cause irreversible changes in the finger, and then, the control system operates the drive 26 to release this pressure. The pressurizing assembly 24 applies a different value of the under-systolic pressure, the pressurizing assembly 22 is operated to perform a further occlusion-release session. During each such occlusion-release session, the light response of the measurement location as a function of time is determined. The effective measurements, i.e., the results that have to be analyzed, are those taken at the state of blood flow cessation.

The operational mode of the device 10 may be such that the control system 14 actuates the measuring unit 20 for performing continuous measurements starting prior to the application of over-systolic pressure. In this case, only those signals, which are associated with the state of blood cessation, are taken into consideration. Measurements taken during the time period prior to the establishment of this state should be disregarded, due to the unavoidable influence of notional and/or other artifacts causing non-monotonic fluctuations of the light transmission. According to an alternative operational mode of the device 10, the control system 14 actuates the measuring unit 20 a small period of time after the application of the over-systolic pressure. During the time period corresponding to the existence of the state of blood cessation, relative light transmission of blood is observed, which reaches its maximum and may last generally from one second to several minutes.

To obtain meaningful results, either at least two timely separated measurement sessions should be considered, at least one of them being that taken during the state of blood cessation, or a single long continuous measurement session should be considered starting after the establishment of the state of blood cessation. During the first measurement session, the control system 14 operates to maintain the cuff 25 and the cushion 29 in their squeezed position, and operates the heating element 32 to heat the finger in the vicinity of the measurement location. The control system 14 then operates the pneumatic drives 26 and 30 to release the pressure. The squeezing action of the cuff 25 is ceased, and after a short delay preset by the respective software in the control unit, the blood flow sharply increases until it reaches new steady state. Then, the control system 14 actuates the second measurement session at a state of the transitional blood flow. The illumination assembly continues to illuminate the finger, but squeezing is halted. The detection assembly, being synchronized by the control system 14, detects the light response of the finger. In other words, the control system 14 selectively operates the measuring unit 20 and the pressurizing assemblies 22 and 24, and analyzes data coming from the measuring unit, as will be described further below.

Figure 2:
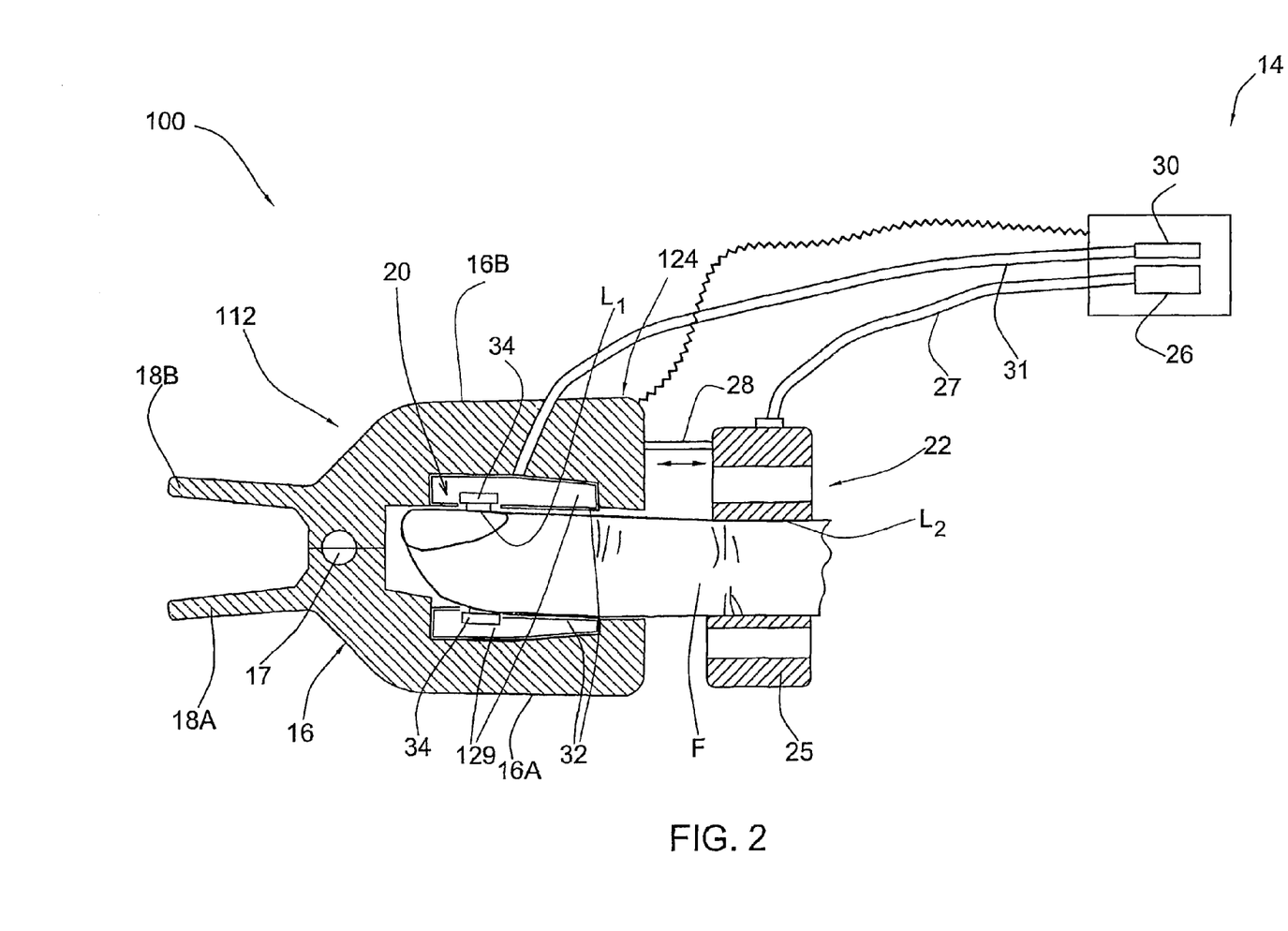
FIG. 2 is a schematic illustration of a probe device according to another embodiment of the invention.

Reference is made to FIG. 2, illustrating a probe device 100 according to another embodiment of the invention. To facilitate understanding, the same reference numbers are used for identifying those components which are common in the devices 10 and 100. The device 100 is constructed generally similar to the device 10, but has a somewhat different design of a finger holder 112. Here, a pressurizing assembly 124 utilizes a cuff-like cushion 129 coupled to a pneumatic drive 30 through a pipe 31. In other words, the second pressurizing assembly 124 is constructed generally similar to the first assembly 22, but is associated with the measurement location $L_1$ for applying under-systolic pressures thereto. The heating element 32 may be attached to the surface of the cushion 129 contacting the finger skin. The operation of the device 100 is similar to that of the device 10. It should, however, be noted, that the pressurizing assembly 124 can be used in combination with the assembly 24 (FIG. 1), rather than replacing it.

Figure 3:
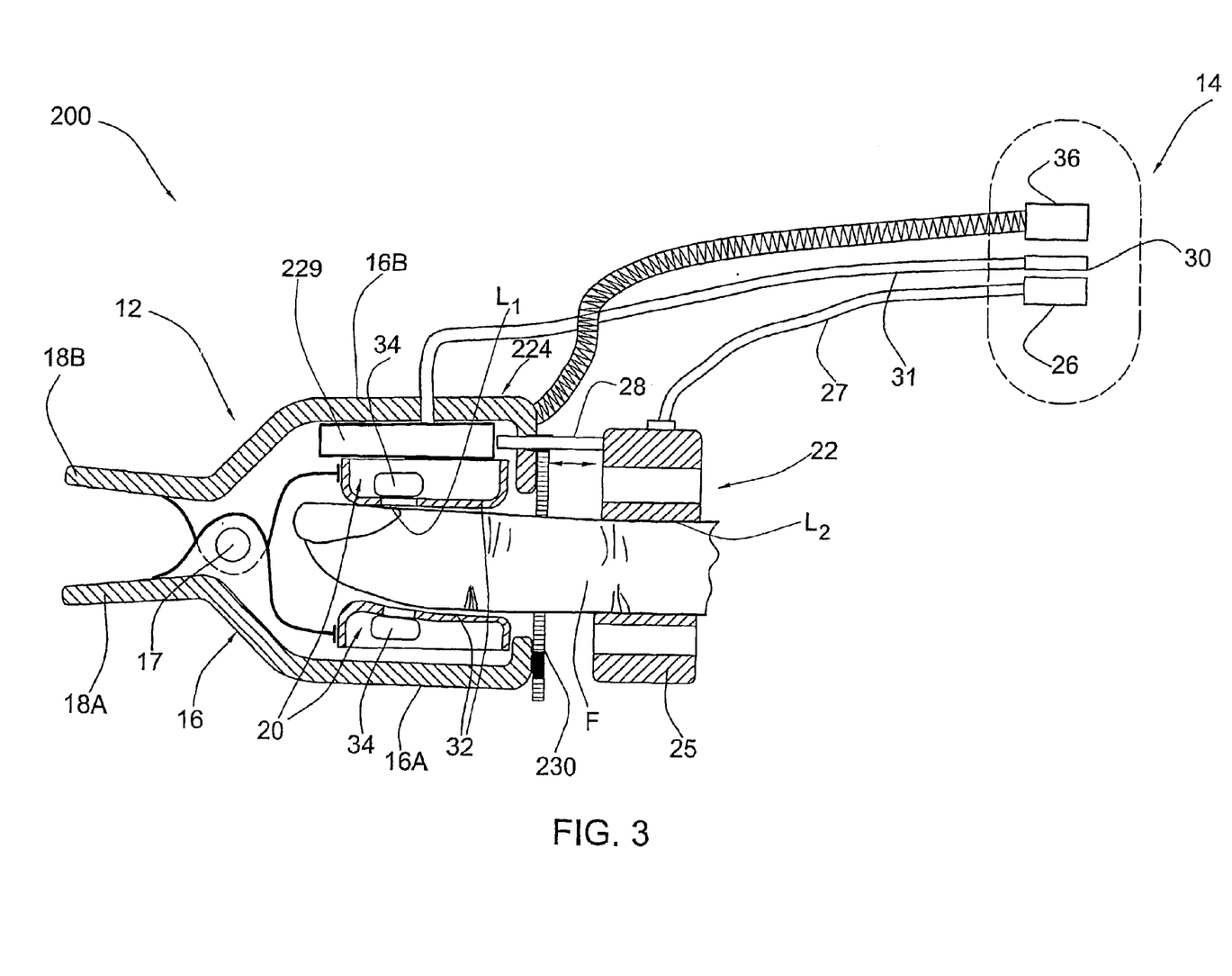
FIG. 3 is a schematic illustration of a probe device according to yet another embodiment of the invention.

FIG. 3 illustrates a probe device 200 having a somewhat different design as compared to the previously described examples. Here, a pressurizing assembly 224, that applies under-systolic pressures to the measurement location $L_1$, includes a balloon-like flat cushion 229, which is accommodated either between the flexible pad 32 and the inner surface of the clamping leg 16B, or inside the pad 32, and is coupled to the drive 30 through the pipe 31. To prevent the opening of the clip member, when in the expanded position of the cushion 229, a lock mechanism 230 is appropriately provided.

It should be noted, although not specifically shown, that the clip member may have a four-legged design, in which case one pair of legs engages the finger at its top and bottom thereof, and the other pair of legs engages the opposite sides of the finger. Such four-sided support of the fingertip prevents its folding at the distal phalanx, thereby avoiding undesirable blood volume changes.

It should also be noted that the rigid connector 28 may be located at either side of the patient's finger. Alternatively, a pair of such connectors can be used located at opposite sides of the finger. Additionally, the processor may be accommodated within the cuff 25, and wires, if any, connecting the processor to the output circuit of the measuring unit 20, may pass through the rigid connector.

Figure 4A:
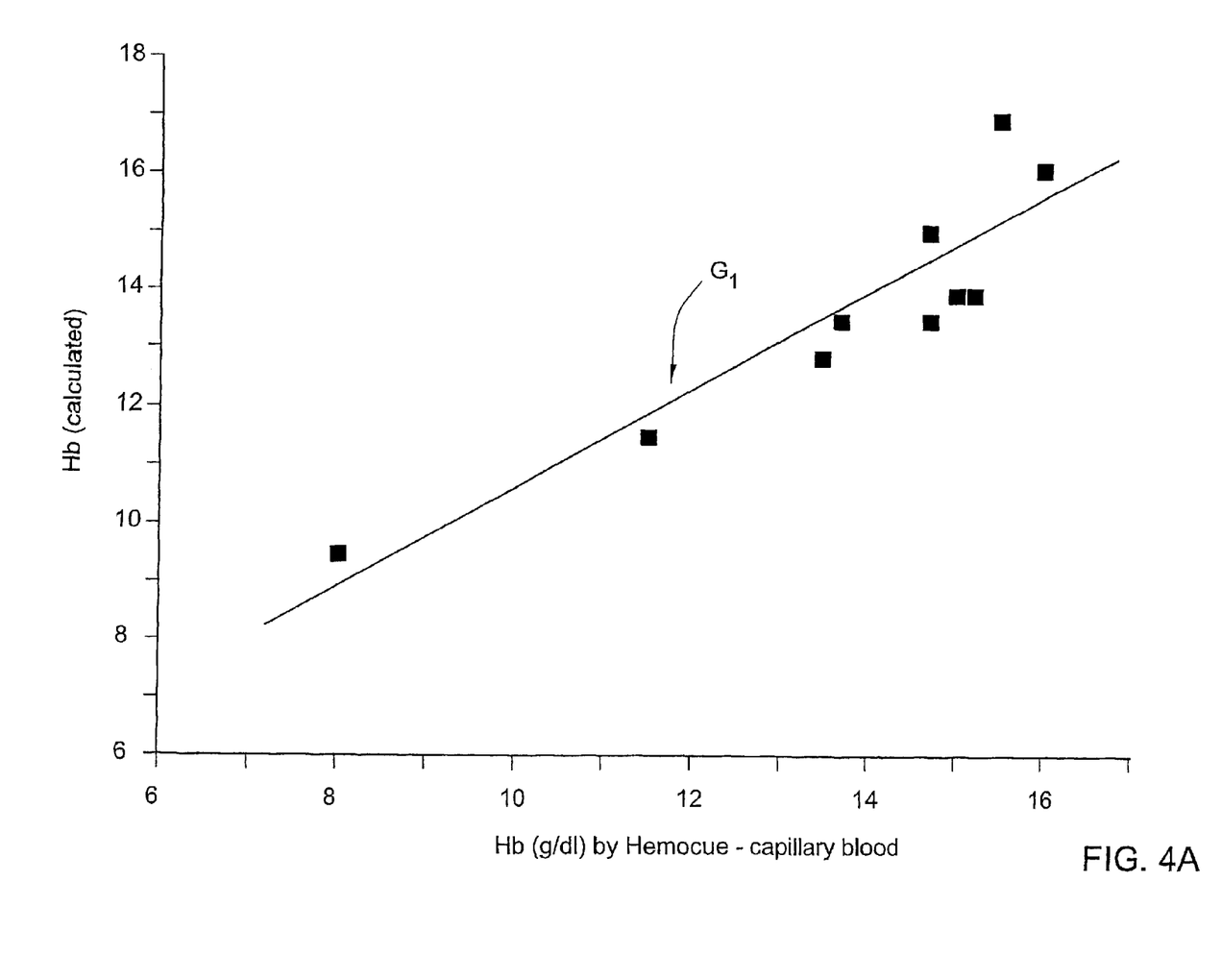
FIGS. 4a to 4d graphically illustrate experimental results obtained with different operational modes of the probe device according to the invention.
Figure 4B:
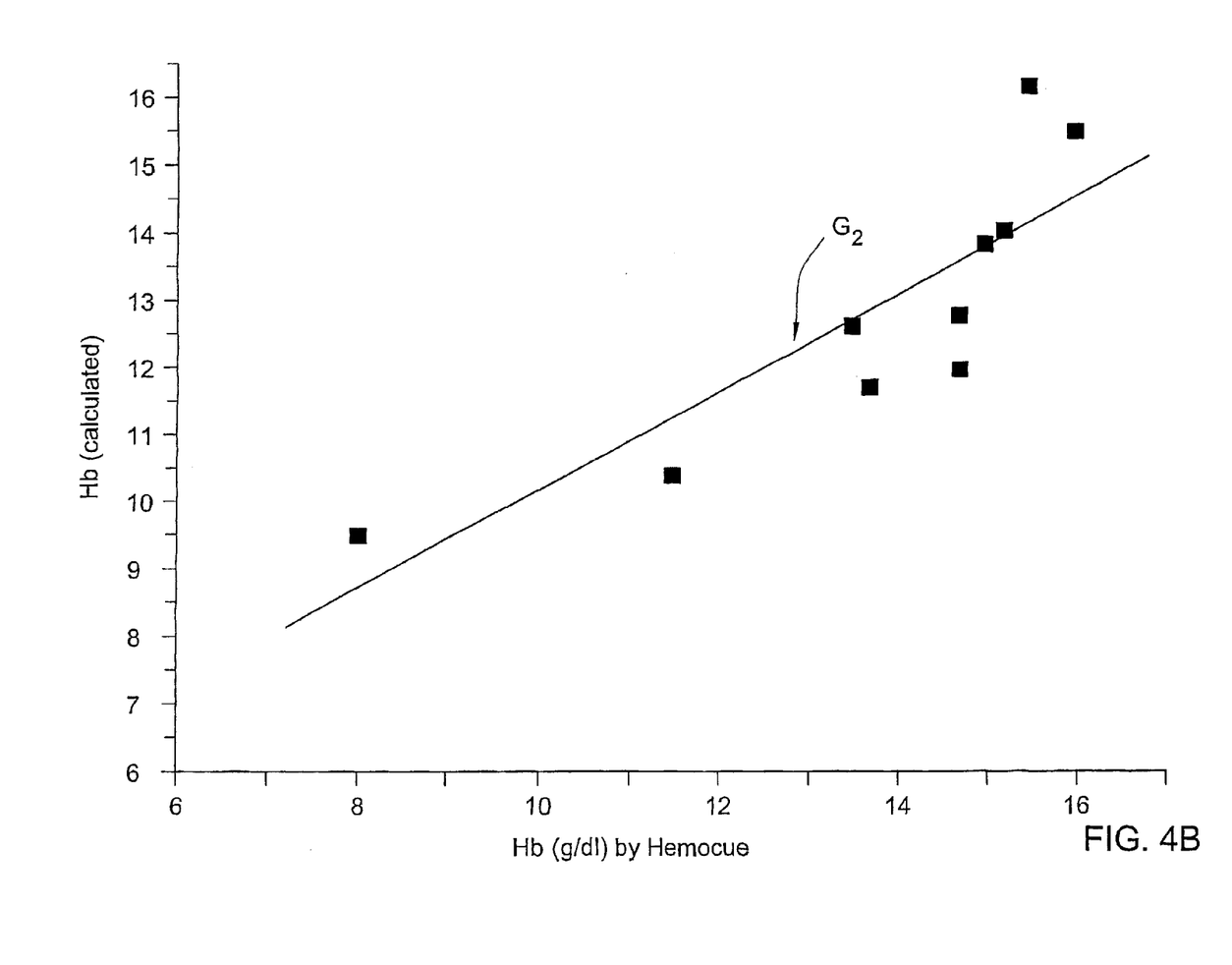

Turning now to FIGS. 4a–4d, the advantageous features of the present invention are graphically illustrated. FIGS. 4a and 4b illustrate, respectively, graphs $G_1$ and $G_2$ presenting experimental results obtained with two different modes of the probe device 10, namely, when the pressurizing assembly 24 is in its active (operational) and passive (non-operational) modes. Each of the graphs $G_1$ and $G_2$ corresponds to the concentration of hemoglobin derived from measurement data obtained with the measurement unit 20 as the function of the hemoglobin concentration obtained with one of the conventional techniques (invasive). To plot each of the graphs, ten measurement points were used. The results show that with the active mode of the pressurizing assembly, when a desired, optimal under-systolic pressure is applied to the measurement location, the measured correlation between the concentration values obtained with different techniques is about 0.91, and the standard deviation is 0.9. While with the passive mode of the pressurizing assembly, these parameters are, respectively, 0.79 and 1.3.

Figure 4C:
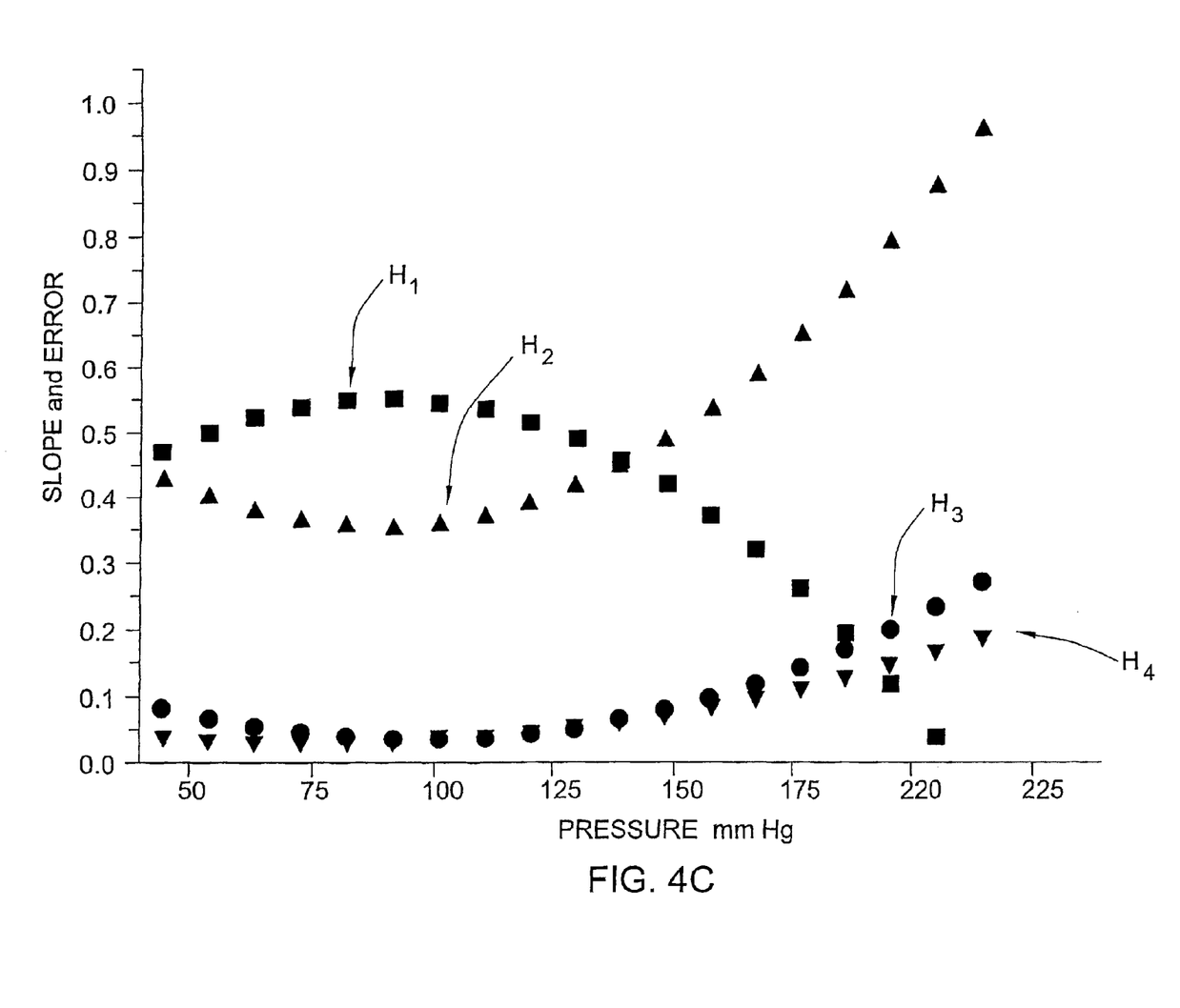
Figure 4D:
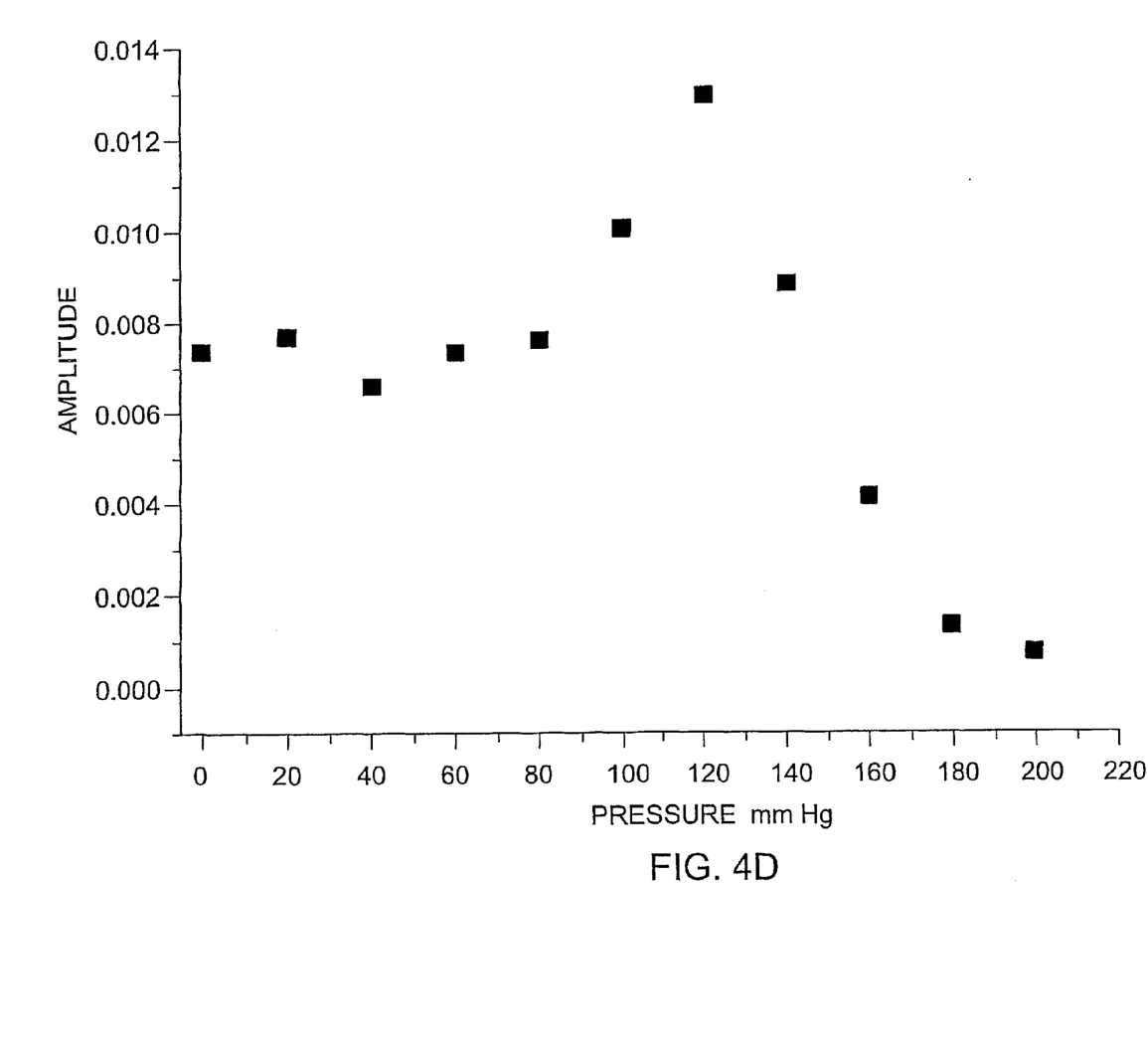

FIGS. 4c and 4d illustrate examples of the technique of the present invention enabling the determination of the desired, optimal pressure to be applied by the pressurizing assembly 24 to a specific patient. FIG. 4c illustrates four graphs $H_1$, $H_2$, $H_3$ and $H_4$. Graphs $H_1$ and $H_2$ correspond to the parametric slopes as functions of the pressure applied by the assembly 24, wherein the parametric slopes were obtained for two different pairs of wavelengths: (1) $\lambda_1=660$ and $\lambda_2=940$ nm, and (2) $\lambda_1=1300$ and $\lambda_2=940$ nm, respectively.

The slope-based technique of determining the blood substance concentration is disclosed in the above-indicated PCT application assigned to the assignee of the present application. A parametric slope is determined as the transmission logarithm at the wavelength $\lambda_2$, i.e., $Log(\lambda_2)$, versus the transmission logarithm at the wavelength $\lambda_1$, i.e., $Log(\lambda_1)$, over a certain time interval (e.g., long occlusion) or at timely separated occlusion stages (i.e., multiple occlusion-release sessions). It should be understood that the slope-based technique may be applied with the pulse-oxymetry as well. In this case such a slope correspond to AC/DC ratio that enables the determination of blood-related parameters. In other words, the parametric slope is a linear function of $Log(\lambda_2)$ versus $Log(\lambda_1)$, whose slope can be determined, for example, by a known linear regression algorithm.

Graphs $H_3$ and $H_4$ correspond to the slope-error (i.e., standard deviation) as the function of pressure, for the above parametric slopes, respectively. To determine the slope-error, several measurement sessions were taken with the same pairs of wavelengths, corresponding parametric slopes were calculated, and standard deviation values were determined. As clearly seen in the figure, the maximum value (0.55) of the slope in graph $H_1$, which represents certain results criteria for the determination of the oxygen saturation, corresponds to the minimum value (0.04) of the respective slope-error in graph $H_3$ at the pressure value of about 100 mmHg. Similarly, the minimum value (0.35) of the slope in graph $H_2$, which represents another results criteria, corresponds to the minimum value (0.04) of the respective slope-error in graph $H_4$ at the pressure value of about 100 mmHg. Thus, this pressure is the optimal pressure for this specific patient, and should be applied to the vicinity of the measurement location on his finger during the optical measurements.

FIG. 4d illustrates the amplitude of the measured signal as the function of the applied pressure. As shown, at a certain pressure value (about 120 mmHg), the amplitude reaches its maximal value.

Hence, the experimental results show that optical parameters of the patient's blood, such as slope and amplitude of the light response, changes with the pressure variations. This enables to select the optimal pressure value (or range) to increase the accuracy of measurements, and obtain better results. Generally speaking, the determination of the optimal pressure value is based on a certain optical criteria, such as minimum of the standard deviation, maximum amplitude of the measured optical signal, AC/DC ratio, parametric slope, etc. It should be understood that the pressure values in the above examples are relevant only for the specific design of the probe used in the experiments, and may be different for different patients and different probe configurations. As indicated above, the rigidity of the constructional elements of the probe also affects the optimal pressure value to be used for optimizing the measurement results.

Those skilled in the art will readily appreciate that various modifications and changes can be applied to the preferred embodiments of the invention as hereinbefore exemplified without departing from its scope defined in and by the appended claims.

What is claimed is:

1. A probe device to be used in non-invasive measurements of a patient's blood parameter, the probe device comprising
    a finger holder having a clip member that secures a fingertip between its clamping legs,
    wherein the finger holder supports a measuring unit for applying measurements to a measurement location on the finger, and carries a pressurizing assembly operable for applying controllably variable pressure to the finger in the vicinity of said measurement location,
    said pressurizing assembly comprising a substantially flat balloon-like cushion coupled to a drive,
    the balloon-like cushion being accommodated between the inner surface of the upper clamping leg and a substantially flexible pad contacting the patient's finger.

2. The probe according to claim 1, comprising a thermo-conductive material at the inner surface the of clip member for heating said measurement location up to desired temperature.

3. A pulse-oxymeter for non-invasive measurements of blood-related parameters of a patient, the pulse-oxymeter comprising the probe device of claim 1 and a control system that operates the pressurizing assembly and the measurement unit and generates data indicative of the measured parameters.

4. The probe according to claim 1, further comprising an additional pressurizing assembly operable for applying over-systolic pressure to a location on the patient's finger upstream of said measurement location with respect to a normal blood flow direction, so as to create a state of blood flow cessation at said measurement location.

5. The probe according to claim 4, wherein said additional pressurizing assembly comprises an air cushion cuff-ring wrapping said location upstream of the measurement location, and a drive coupled to the cuff-ring so as to apply said over-systolic pressure to the upstream location.

6. The probe according to claim 5, further comprising a substantially rigid connector between the clip member and an element of the additional pressurizing assembly located at said upstream location on the finger, the connector being adapted to engage the finger along its middle phalanx and proximal intephalangeal joint, thereby preventing it from folding during the measurements.

7. The probe according to claim 6, wherein said connector allows for reciprocating movement of said element of the additional pressurizing assembly along the finger with respect to the clip member.

8. The probe according to claim 4, wherein said measuring unit, and the pressurizing assemblies are operated by a control system, having a processor for receiving and analyzing data coming from the measuring unit and indicative of the measured light response of the finger.

9. The probe according to claim 1, wherein said pressurizing assembly is associated with manipulating arms of the clip member, such as to controllably vary pressure of the clamping legs onto the fingertip secured therebetween.

10. A method of non-invasive optical measurement of at least one parameter of the patient's blood, the method comprising:

(a) applying the probe device of claim 1 to the patient's blood perfused fleshy medium;

(b) operating the measurement unit for performing several measurement sessions on the measurement location on said medium to detect light response of the medium and generate measured data indicative thereof, and simultaneously operating the pressurizing assembly to vary the pressure applied to the vicinity of said measurement location, wherein each measurement session utilizes at least two different wavelength of incident light;

(c) analyzing the light response of the medium corresponding to different wavelengths of the incident light and different pressure values, and determining an optimal pressure value, so as to utilize the corresponding light response of the medium for deriving therefrom said at least one blood parameter.

11. The method according to claim 10, wherein said optimal pressure value is determined as the pressure value corresponding to certain optical criteria results.

12. The method according to claim 11, wherein the criteria results utilize at least one of the following parameters: minimum of standard deviation, maximum of the amplitude of the light response, AC/DC ratio, parametric slope.

13. A measurement device for the non-invasive measurement of patient's blood parameters, the device comprising:

a finger holder for attaching to the patient's finger, wherein the finger holder is in the form of a clip member, which secures a fingertip between its clamping legs and supports a measuring unit in a manner allowing to apply measurements to a measurement location on the finger;

a first pressurizing assembly operable for applying oversystolic pressure to a location on the patient's finger upstream of said measurement location with respect to a normal blood flow direction, so as to create a state of blood flow cessation at said measurements location;

a second pressurizing assembly associated with the finger holder and operable for applying desired pressure to the finger in the vicinity of said measurement location, said second pressurizing assembly comprising a substantially flat balloon-like cushion coupled to a drive and accommodated between the inner surface of the upper clamping leg and a substantially flexible pad contacting the patient's finger; and a control system selectively operating the first and second pressurizing assembly, and selectively operating the measuring unit, the control system having a processor that received data indicative of measured signals coming from the measuring unit and analyzes said data.

* * * * *